US006605265B1

(12) United States Patent
Schirmann et al.

(10) Patent No.: US 6,605,265 B1
(45) Date of Patent: Aug. 12, 2003

(54) CONTINUOUS PRODUCTION OF AZINES/HYDRAZINE HYDRATE

(75) Inventors: Jean-Pierre Schirmann, Oullins (FR); Jean-Pierre Pleuvry, La Barthe de Neste (FR); Pierre Tellier, Saint Foy les Lyon (FR)

(73) Assignee: Atochem, Put Eaux (FR)

( * ) Notice: Subject to any disclaimer, the term of this patent is extended or adjusted under 35 U.S.C. 154(b) by 0 days.

(21) Appl. No.: 08/217,752

(22) Filed: Mar. 25, 1994

Related U.S. Application Data

(63) Continuation of application No. 07/998,763, filed on Dec. 30, 1992, now abandoned, which is a continuation of application No. 07/528,097, filed on May 24, 1990, now abandoned.

(30) Foreign Application Priority Data

May 24, 1989 (FR) .............................................. 89 06803

(51) Int. Cl.[7] ........................ C01B 21/16; C07C 241/00; C07C 241/02
(52) U.S. Cl. ....................................... 423/407; 564/249
(58) Field of Search ................................ 423/406, 407, 423/43; 564/249

(56) References Cited

U.S. PATENT DOCUMENTS

| 3,869,541 A | * | 3/1975 | Weiss et al. ................. 423/407 |
| 3,972,878 A | | 8/1976 | Schirmann et al. .......... 564/249 |
| 4,005,179 A | * | 1/1977 | Eichenhofer et al. ........ 423/407 |
| 4,013,758 A | * | 3/1977 | Osborg ........................ 423/407 |
| 4,093,656 A | * | 6/1978 | Schirmann et al. .......... 564/249 |
| 4,628,119 A | * | 12/1986 | Nawata et al. ............... 423/407 |
| 4,725,421 A | * | 2/1988 | Schirmann et al. .......... 423/407 |
| 4,888,160 A | * | 12/1989 | Kosin et al. ................. 423/430 |

FOREIGN PATENT DOCUMENTS

| DE | 2326197 | 12/1974 |
| EP | 0179699 | 4/1986 |

OTHER PUBLICATIONS

"Phase Aqueuse", published in Sep. 1984. (Hydrative Hydrate A to Chem, Paris France).
Chemical Abstract, vol. 100, No. 24042z.

* cited by examiner

*Primary Examiner*—Wayne A. Langel
(74) *Attorney, Agent, or Firm*—Burns, Doane, Swecker & Mathis, L.L.P.

(57) ABSTRACT

Azines, e.g., ketazines, are continuously produced by (i) establishing a loop having an azine reaction medium circulating therein, such loop including an azine reaction zone, means for separating azine final product from the circulating reaction medium, means for heating the reaction medium and for purging water therefrom, and means for recycling heated and purged reaction medium to the azine reaction zone, (ii) introducing hydrogen peroxide, ammonia and a carbonyl compound into the circulating reaction medium in the azine reaction zone, (iii) withdrawing azine final product thus formed from the circulating reaction medium. downstream of the azine reaction zone, (iii) thereafter purging water from the circulating reaction medium to maintain the volume thereof essentially constant, (iv) heating the circulating reaction medium to a temperature of at least 130° C., (v) recycling thus heated reaction medium to the azine reaction zone, and (vi), at any point along the loop, introducing a reagent into the circulating reaction medium as to essentially maintain the equilibrium of the azine-forming reaction; the final product azines are conveniently hydrolyzed into hydrazine hydrate.

23 Claims, 1 Drawing Sheet

CONTINUOUS PRODUCTION OF AZINES/HYDRAZINE HYDRATE

This application is a continuation, of application Ser. No. 07/998,763, filed Dec. 30, 1992 adandoned, which is Continuation Application of U.S. Ser. No. 07/528,097, filed May 24, 1990 abandoned.

BACKGROUND OF THE INVENTION

1. Field of the Invention

The present invention relates to the synthesis of azines and to the production of hydrazine hydratetherefrom.

2. Description of the Prior Art

Hydrazine, which typically exists in the form of hydrazine hydrate, is a compound which is very widely used, inter alia, as an intermediate for numerous syntheses. According to Kirk Othmer, 3rd edition, volume 12, pages 734 to 755, hydrazine is produced either by the oxidation of ammonia using chlorine or bleach and optionally a ketazine intermediate, or by the reaction of hydrogen peroxide, ammonia and a ketone.

The peroxide process has been described in numerous patents, in particular U.S. Pat. Nos. 3,972,878, 3,972,876, 3,869,541, 3,948,902, 3,919,256, 3,943,152 and 4,093,656. Kirk Othmer, supra, describes the principle of the process according to U.S. Pat. No. 4,093,656. Thus, hydrogen peroxide, ammonia and methyl ethyl ketone are reacted in the presence of acetamide and sodium phosphate to prepare, after separation, the corresponding azine and an aqueous solution (the working solution) containing acetamide and sodium phosphate. This aqueous solution is concentrated to remove the water produced by the reaction, as well as the water contributed by the hydrogen peroxide, and then is recycled to the reactor. The azine is hydrolyzed to hydrazine, and the methyl ethyl ketone is recovered and recycled to the reactor (for the synthesis of the azines).

When such a process is carried out continuously, a lessening of activity is observed in the working solution or reaction medium, i.e., a lowering of productivity of the reactor, and it is thus necessary to formulate a new working solution (reaction medium).

U.S. Pat. No. 4,093,656 describes several examples of different working solutions.

In the prior art noted above, it is indicated that, although the process of azine synthesis can be carried out using the reagents in widely varying proportions, variations in the production yield of azines can be observed. Hence, it is advantageous to maintain certain proportions in the reaction mixture, in particular for the compounds contained in the working solution.

SUMMARY OF THE INVENTION

Accordingly, a major object of the present invention is the provision of an improved process for the preparation of azines, which improved process is far simpler than those to date characterizing the state of this art and which permits of the continuous and constant production of azine without requiring stringent monitoring of the working solution (reaction medium).

Briefly, the present invention features a process for the synthesis of azines from hydrogen peroxide, ammonia and a reagent having a carbonyl group, comprising:

(a) contacting such reagents with a solution, designated the working solution or reaction medium, until the azine is produced;

(b) (i) separating the azine and optionally the excess of carbonylated reagent from (ii) the working solution;

(c) increasing the temperature of all or a portion of the working solution to a value greater than 130° C., with the water produced by the reaction being eliminated either before, after or concomitantly with such temperature increase;

(d) recycling the working solution to step (a); and (e) introducing a compound adapted to maintain the production of the azine into the working solution during at least one of the above steps (a) to (d).

BRIEF DESCRIPTION OF THE DRAWING

The FIGURE of Drawing is a schematic/diagrammatic illustration of one embodiment of the process/apparatus, according to the present invention.

DETAILED DESCRIPTION OF THE PREFERRED EMBODIMENTS OF THE INVENTION

Figure 1:
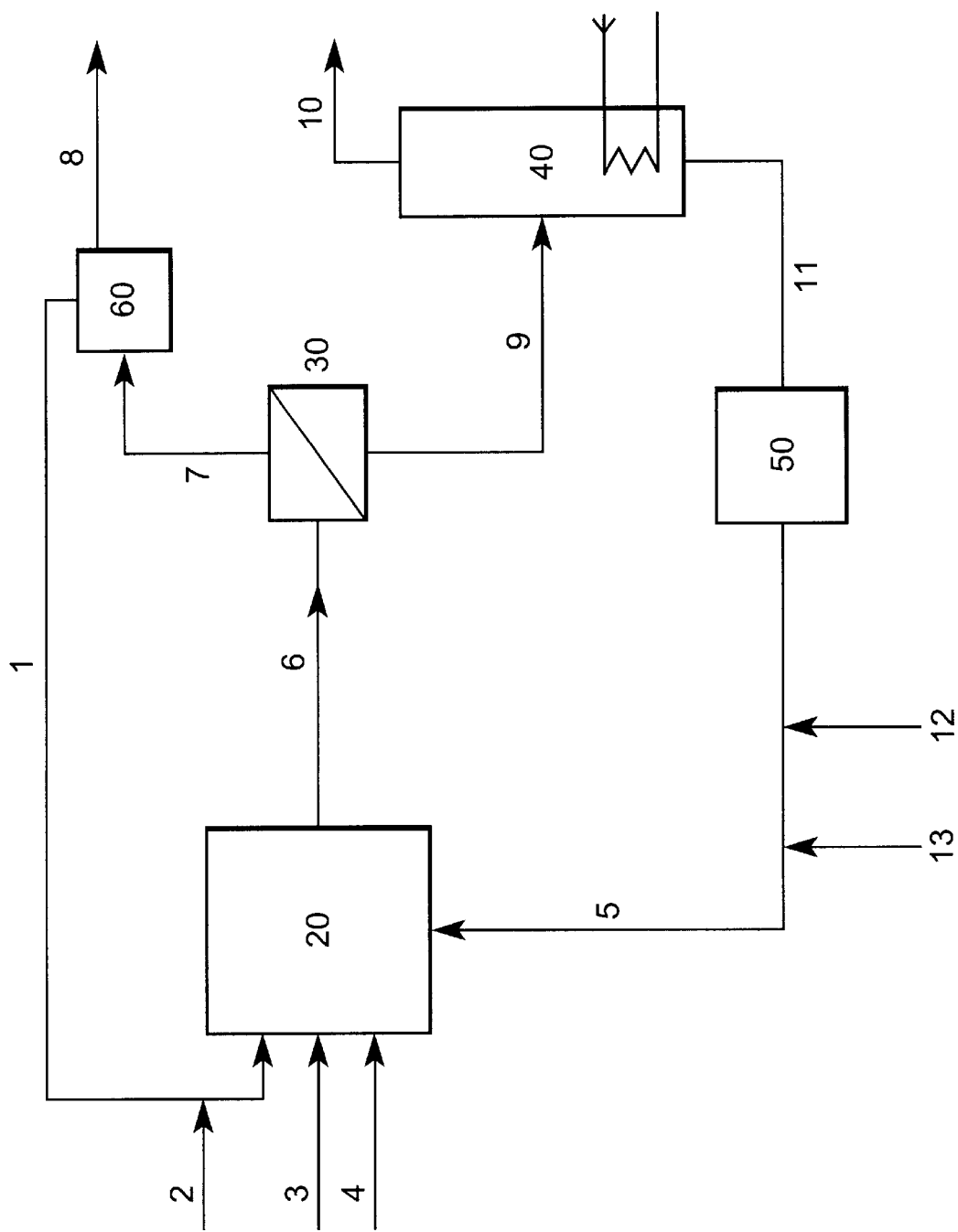

More particularly according to the present invention, the basic reaction for the preparation of the azines can be represented as follows:

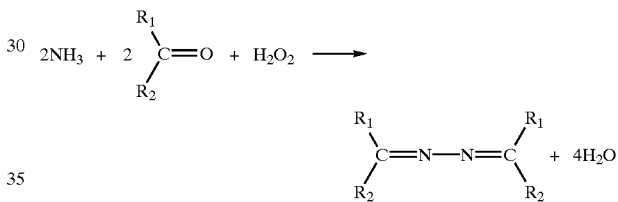

The hydrogen peroxide may be used in its typical commercial form, for example as an aqueous solution containing 30% to 90% by weight of $H_2O_2$. Advantageously, one or more of the normal stabilizers for peroxide solutions may be added, for example phosphoric, pyrophosphoric, citric, nitrilotriacetic or ethylenediaminetetraacetic acid, or the ammonium or alkali metal salts of such acids. The amount to be used advantageously ranges from 10 to 1,000 ppm and preferably from 50 to 250 ppm of the total amount of reagents and reaction medium introduced into the reactor.

The ammonia may be anhydrous or an aqueous solution thereof.

The reagent having a carbonyl function is of the formula:

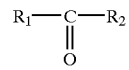

in which $R_1$ and $R_2$, which may be identical or different, are each hydrogen, an alkyl radical having from 1 to 12 carbon atoms, a branched alkyl or cycloalkyl radical having from 3 to 12 carbon atoms, or an aromatic radical having from 6 to 12 carbon atoms, with the proviso that $R_1$ and $R_2$ may together form a linear or branched alkylene radical having from 3 to 12 carbon atoms; the above radicals may either be unsubstituted or substituted with at least one halogen or $NO_2$, hydroxy, alkoxy or carboxylic ester group, and preferably Cl, $NO_2$ or $CH_3O$.

Exemplary of the reagents of the formula:

are the aldehydes and ketones.

Representative such aldehydes include formaldehyde, acetaldehyde, butyraldehyde, isobutyraldehyde, n-pentanal, pivalaldehyde, benzaldehyde, monochlorobenzaldehyde, para-nitrobenzaldehyde, anisaldehyde, β-chloropropionaldehyde, and β-methoxypropionaldehyde.

Representative such ketones include acetone, 2-butanone, 2-pentanone, 3-pentanone, methyl isopropyl ketone, methyl isobutyl ketone, methyl ethyl ketone, methyl cyclohexyl ketone, acetophenone, benzophenone cyclobutanone, cyclopentanone and cyclbhexanone.

Advantageously such ketones are used in which $R_1$ and $R_2$, which may be identical or different, are each a linear or branched alkyl radical having from 1 to 5 carbon atoms, preferably acetone, methyl ethyl ketone and methyl isobutyl ketone.

The azine may be hydrolyzed into hydrazine hydrate according to the reaction:

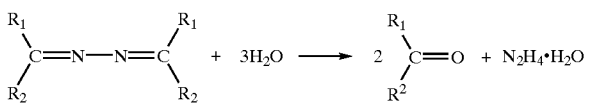

thus regenerating the carbonyl reagent:

which is recycled to the reactor.

It is also within the scope of the invention to use mixtures of aldehydes, of aldehydes and ketones, or of ketones. For example, a mixture of:

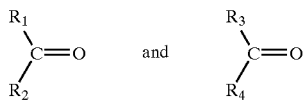

may be used, wherein $R_3$ and $R_4$ have the same definitions as $R_1$ and $R_2$, and such mixtures may also contain:

Mixtures of symmetrical and asymmetrical azines of the following formulae may thus be used:

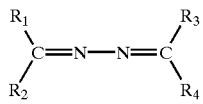

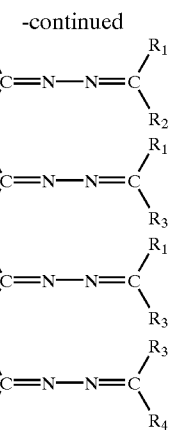

As indicated above, the mixture of ketones or aldehydes is regenerated by hydrolysis.

The hydrolysis reaction of ketazines is described in U.S. Pat. Nos. 4,724,133 and 4,725,421.

The reagents may be used in stoichiometric amounts; however, 0.2 to 5 moles, and preferably 1.5 to 4 moles of the carboxylated reagent (aldehyde or ketone), and 0.1 to 10 moles, and preferably 1.5 to 4 moles of ammonia, are used per mole of hydrogen peroxide.

The amount of working solution (reaction medium) ranges from 0.1 to 1 kg per mole of hydrogen peroxide. The quality of the working solution, namely, its catalytic strength or its activity permitting the reagents to be converted into the azine, depends on the treatment of step (c) and on the compound employed in step (e).

The proportions of reagents given above permit a total conversion of hydrogen peroxide to be attained together with a yield of azine corresponding to morethan 50% of the hydrogen peroxide converted, and even up to a yield of 90%.

The reaction medium is any solution provided that it can contain water produced by the reaction and transfer it to step (c). The composition of this solution is not empirically known, and this is precisely the advantage of the process of the invention vis-a-vis the prior art processes. An initial working solution is formulated to initiate start up of the production installation, then, after production has commenced, the treatment (c) and the introduction of the compound in step (e) ensure that the working solution is suitable for the production of azines. The volume of the working solution is monitored, and can be adjusted by eliminating more or less water at (c). Its activity is monitored by measuring the production of azine.

The formulation of the initial reaction medium will be described hereinafter, during the discussion of the step (e).

The hydrogen peroxide, the ammonia and the carbonylated reagent may be contacted with the working solution in any manner.

Advantageously, the procedure is carried out in a homogeneous medium, or in a medium which ensures at least sufficient solubilization of the reagents required for the azine production. The reaction can be carried out over a very wide temperature range, for example ranging from 0° to 100° C. It is advantageously carried out at a temperature ranging from 30° to 70° C. Although it can be carried out at any pressure, it is simpler at atmospheric pressure, but the pressure can increase to about 10 bars if this is necessary to maintain, as is preferable, the reaction of step (a) in the liquid phase.

The reagents can be introduced simultaneously or separately, and in any order, into the working solution. Many types of reactors can be used, whether stirred or unstirred, or even those of small capacities which can be arranged in parallel or in series and operated either co-currently or countercurrently, or any combination of the above.

The azine (i) and optionally the excess of carbonylated reagent is separated from (ii) the working solution by any known methods, such as liquid/liquid extraction, distillation or any combination thereof.

The azine and the excess of carbonylated reagent may form a homogeneous phase, or be only partially miscible. It is advantageous to separate these before hydrolyzing the azine. This excess of carbonylated reagent, together with that which is recovered after hydrolysis of the azine, may be recycled to the reactor. It ammonia is in excess at step (a), it is entrained with the water produced by the reaction in the working solution.

The treatment of step (c) entails, for all or a portion of the working solution in (i), eliminating the water produced by the reaction and (ii) increasing the temperature thereof to a value greater than 130° C.; (i) and (ii) may be carried out in any order, or simultaneously.

The elimination of the water is a typical operation which may advantageously be carried out in a distillation column, while ensuring recovery of those compounds which are more volatile than water. Among such compounds which are more volatile than water and which evolve are ammonia, a minor amount of the carbonyl reagent if such a lighter-than-water compound has been used in step (a), and methanol or ethanol if the working solution is comprised thereof.

The ammonia, and if present, the carbonylated compound, are returned to the reactor. The methanol or ethanol, after separation from the water, are recycled to step (a) in the reactor or mixed with the working solution at the outlet from step (c). The treatment above 130° C. may be carried out in a heat exchanger or a reboiler at the base of the column.

Advantageously, the working solution is adjusted to a temperature which is at least equal to 130° C., while simultaneously eliminating the water produced by the reaction. Preferably, the temperature of the working solution is adjusted to a value ranging from 150° to 250° C., and more preferably from 170° to 230° C. This operation can be carried out in any one of a number of ways; it is advantageous to use a container provided with a heating system, such container being surmounted by a distillation means, which may be a distillation column or any apparatus providing the same function. The container/distillation column assembly is charged with the working solution, which enters the distillation column. In a preferred embodiment of the invention, the apparatus for this step (c) is a distillation column, the base of this column (the lower part) being maintained at at least 130° C., and this column is charged from the side with the working solution. The pressure of this column is adjusted by the usual methods, such as the flow rate of the coolant in the reflux condenser or the vacuum system, in order to ensure boiling at the base, and the column is classified such that the water and the compounds which are more volatile than water are transported to the top. The rate at which the water is drained off from the head of the column is such that a constant volume of the working solution is ensured. Among the compounds which are more volatile than water, and which evolve, are ammonia, a minor amount of the carbonylated reagent if such a lighter-than-water compound has been used at step (a), and methanol or ethanol if the working solution contains these.

The ammonia and, if present, the carbonylated compound, are returned to the reactor. The methanol or ethanol, after separation from the water, are recycled to step (a) in the reactor or mixed with the working solution at the outlet from step (c). In a preferred embodiment of the invention, the column comprises from 5 to 50 theoretical plates, and is fed between the 3rd and the 20th plate, counting from the base of the column.

In a preferred embodiment of the invention, wherein a distillation column is used, the temperature of the reaction medium which is charged into the column is less than 110° C., the temperature of the base of the column ranges from 150° to 250° C. and the residence time ranges from 10 minutes to 2 hours. In such preferred embodiment, the feed temperature advantageously ranges from 50° to 110° C., the temperature of the base of the column ranges from 170° to 230° C. and the residence time ranges from 10 minutes to a few hours.

It is not necessary to treat the entirety of the working solution at step (c); at the end of step (b) only a portion of the solution may be treated, and the portion of the solution which has been treated may then be mixed at (c) with the untreated portion and the entirety returned to the reactor at step (a).

Advantageously, the portion which indeed is treated constitutes at least 50% by weight of the entire mass of the working solution, and preferably 60% to 100%, according to the activity of this solution necessary for the production of azines.

One advantage of the process of the present invention is that the installation is filled with an initial working solution, which is then circulated therein, treated at step (c) and introducing therein a compound which maintains the production of the azine. The compound of step (e) is advantageously an organic or inorganic oxyacid, an ammonium salt thereof, or in general, a derivative thereof: an anhydride, ester, amide, nitrile, acyl peroxide, or mixture thereof. Preferably, either the amides, ammonium salts or nitriles are thus used.

Exemplary of such compound are (i) amides of carboxylic acid of the formula $R_5COOH$, in which $R_5$ is hydrogen, a linear alkyl radical having from 1 to 20 carbon atoms, or a branched or cyclic alkyl radical having from 3 to 12 carbon atoms, or a phenyl or substituted phenyl radical, (ii) amides of polycarboxylic acids of the formula $R_6(COOH)_n$, in which $R_6$ is an alkylene radical having from 1 to 10 carbon atoms and n is equal to 1 or 2; $R_6$ may also be a simple chemical bond, in which case n equals 2. The radicals $R_5$ and $R_6$ may be substituted with halogens or OH, $NO_2$ or methoxy groups. The amides of organoarsenic acids are also exemplary.

The preferred amides are formamide, acetamide, monochloroacetamide and propionamide.

Among the ammonium salts, salts of hydracids, inorganic oxyacids, arylsulfonic acids, $R_5COOH$ acids or $R_6(COOH)_n$ acids, wherein $R_5$, $R_6$ and n are as defined above, and organoarsenic acids are advantageously used.

The preferred ammonium salts are the formate, acetate, monochloroacetate, propionate, phenylarsonate and cacodylate.

Among the nitriles, the compounds of the formula $R_7(CN)_n$, in which n may range from 1 to 5 according to the valency of $R_7$ and $R_7$ is a cyclic or acyclic alkyl radical having from 1 to 12 carbon atoms, or benzene or pyridine, are representative. $R_7$ may be substituted with substituents which are not oxidized in the reactor at step (a), for example halogens or carboxylic, carboxylic ester, nitro, amine, hydroxy or sulfonic acid groups.

The preferred nitriles are acetonitrile and propionitrile.

The working solution (reaction medium) is constituted by dissolving one or more compounds selected from among such organic or inorganic oxyacids, their ammonium salts, or, in general, any derivative thereof: anhydrides, esters, amides, nitriles or acyl peroxides, or a mixture thereof. Advantageously, the above amides, ammonium salts or nitrites are thus used.

This solution may be aqueous, or based on an alcohol, or a mixture of alcohol and water. Among the alcohols, the saturated aliphatic alcohols having from 1 to 6 carbon atoms, and preferably 1 to 2 carbon atoms, are advantageously used.

Diols, and more particularly diols having from 2 to 5 carbon atoms, are also advantageously used. Exemplary thereof are glycol, propyleneglycol, 1,3-propanediol, 1,3- and 1,5-pentanediol.

Circulation of this working solution between the reactor at (a), separation at (b), treatment at (c) and return to (a) is initiated. The cycle thus first operates "empty", i.e., without the production of azine, and then the progressive introduction of reagents into the reactor at step (a) is begun. As soon as the production of azine is established, a compound capable of maintaining the production of azine, advantageously selected from among the amides, ammonium salts or nitriles, is introduced continuously.

Whether it is to form the initial working solution or for the complement:at step (e), it is also within the scope of the invention to form the ammonium salt in situ using the ammonia, it being sufficient to use the corresponding carboxylic acid. For example, an ammonium acetate complement may be replaced with an acetic acid complement; in the same manner, to constitute the initial working solution, it is sufficient to work "empty", that is to say, without the hydrogen peroxide but with the ammonia. Then, as above, this working solution being formed is circulated and afterwards production is initiated by adding the reagents, i.e., ammonia, hydrogen peroxide and the carbonylated compound. The amount of amide, acid, ammonium salts or nitrile to be added to the water, the alcohol or the mixture of water and alcohol ranges from 40% to 80% by weight of the working solution at the beginning of step (a).

This amount is expressed as the acetic acid equivalent, namely, one mole of ammonium acetate, or one mole of propionamide, or one mole of acetonitrile, or one mole of formamide, are equivalent to one mole of acetic acid. It is possible to add only the amide, the ammonium salts or the nitrile, or a mixture of two or all three of these compounds, it being appreciated that one of them may itself be a mixture (of several amides, several ammonium salts or several nitrites).

Advantageously, the initial working solution is formed by diluting the ammonium salt in water to about 50% by weight, and preferably it is formed in situ from acetic acid. As regards the introduction of the compound of step (e), any compound or any mixture of the above amides, ammonium salts or nitriles may be used. Any compound which forms the ammonium salt in situ, for example acetic acid, may also be used. The amount is adjusted as a function of the production of azine. Those skilled in this art may easily determine the amount to be added to maintain the production of azine. The mechanism of this synthesis is not known, nor is the contribution of step (c) and step (e) in the process of the invention for the production of azines.

It is generally observed that at most 1% by weight with respect to the working solution present at step (a) is sufficient.

There is no relationship between the compound which is used to form the initial working solution and the compound which is introduced at step (e); any combination may be used. Advantageously, the working solution is constituted of an ammonium salt formed in situ or a nitrile, and the compound of step (e) is a nitrile or a $R_5COOH$ or $R_6(COOH)_n$ carboxylic acid. Preferably, the working solution is comprised of acetic acid and ammonia, and acetic acid is introduced at step (e).

In a preferred embodiment of the invention, certain high boiling point impurities may be eliminated from the working solution. It suffices to thus treat the entirety or a fraction of the working solution, and advantageously the portion of the working solution which emerges from step (c) is purified. The elimination of these high boiling point impurities may very simply be carried out by distillation, completely or partially rejecting everything which boils, above the component (or its salts) used to formulate the working solution or to maintain its activity (or of the heaviest compound in the case of a mixture). This amount of impurities represents from 0.01% to 5% by weight of the entirety of the working solution.

This amount is small and may depend on the conditions of the azine synthesis and on the impurities already present in the ammonia, the hydrogen peroxide and the carboxylated compound; it is known that, in the presence of impurities, hydrogen peroxide may give rise to heavy impurities.

In lieu of distillation, these impurities may also be eliminated from the working solution by passing the latter over absorbent substances constituted of microporous particles. For example, the materials described in U.S. Pat. No. 4,657,751 may be used.

In another preferred embodiment of the invention, a catalyst assuring the stabilization of the azine synthesis reaction may be added to the working solution between step (c), or to the reaction at step (a). This catalyst advantageously has the general formula Q—X—Y=Z, in which Q is hydrogen or an alkali metal or ammonia; X and Z are oxygen or nitrogen atoms and Y is a carbon, nitrogen, arsenic, antimony, phosphorus, sulfur, selenium or tellurium atom; and the atoms X, Y and Z bear the necessary substituents to satisfy all valencies. This Q—X—Y=Z catalyst may be a phosphate, phosphite, phosphonate, polyphosphate, pyrophosphate, arsenate, phenylarsenate, cacodylate, bicarbonate, antimonate, stannate or sulfate of ammonia or alkali metals. The corresponding esters, in particular those of aliphatic alcohols having from 1 to 5 carbon atoms, may also be used. The amount to be used advantageously ranges from 10 to 1,000 ppm, and preferably from 50 to 250 ppm of the total amount of the working solution and the reagents at step (a). The alkali metal phosphates and disbdium orthophosphate are the preferred.

Shown in the FIGURE of Drawing is one embodiment of the present invention. The step (a) is carried out in reactor 20, the azine is separated from the reaction medium in decanter 30, the azine is hydrolyzed in vessel 60, step (c) is carried out in column 40, and the heavy impurities are removed by the ion exchange resin in the exchanger 50. To simplify the diagram, the pumps, the valves and the reflux system of column 40 have not been shown.

Line 1 constitutes the methyl ethyl ketone (MEK) recycling system, the complement of MEK is introduced via inlet 2, the hydrogen peroxide feed is introduced via line 3, the ammonia via line 4 and the working solution via line 5. The mixture of azine and the working solution is withdrawn via line 6 and is separated in the decanter 30. The azine is transferred via line 7 to the hydrolysis vessel 60 and hydrazine is withdrawn via outlet 8, with the MEK being recycled via line 1 to the reactor 20. The working solution is transported to column 40 by line 9, from which water and a minor amount of ammonia are recovered through outlet 10. The remainder of the working solution is transferred via line 11 to the exchanger 50 and therein is passed over absorbent polystyrene resins having a pore volume of 51%, a surface area of 750 m$^2$/g, the mean diameter of the pores of which is 50 Å and the particle size 1.2 to 0.3 mm (20 to 50 mesh). It is then recycled to reactor 20 via line 5. Acetic acid is added at inlet 12 according to step (e) of the process and disodium phosphate is added at inlet 13.

In order to further illustrate the present invention and the advantages thereof, the following specific examples are given, it being understood that same are intended only as illustrative and in nowise limitative.

EXAMPLE 1

The operation was carried out in the apparatus shown in the FIGURE of Drawing, except that 30% by weight of the working solution in line 9 was not treated in the column 40, but was diverted to the treated portion thereof down-stream of the exchanger 50. The working solution was constituted, by mixing water, acetic acid and ammonia, while heating column 40 gradually. The amount of acetic acid used to produce the ammonium acetate represented about 50% by weight of the working solution. In a static state, the following conditions were established:

(i) a complement of 100 kg/h methyl ethyl.ketone (MEK) was introduced via inlet 2;

(ii) 1,000 kg/h H$_2$O$_2$ stabilized with EDTA, expressed as 100% H$_2$O$_2$ (in the form of a 70% solution), were introduced via inlet 3;.

(iii) 1,000 kg/h NH$_3$ were introduced via inlet 4;

(iv) 3 kg/h disodium phosphate were introduced via inlet 13;

(v) 60 kg/h acetic acid were introduced via inlet 12;

(vi) the reactor 20 was operated at 50° C.;

(vii) the flow rate of the working solution was 11,000 kg/h in line 5;

(viii) a flow rate of 3,900 kg/h MEK-azine CH$_3$(C$_2$H$_5$)C=N—N=C(C$_2$H$_5$)CH$_3$ was established in line 7; and (ix) the working solution at 50° C. was charged into column 40 at the 11th plate above the boiler, there being 19 plates between the feed and the head. The head pressure of column 40 was 0.9 bar absolute, the base was at a temperature of 180° C. and the boiler was charged with 10,500 kg/h steam at 18 bars absolute.

EXAMPLE 2

The operation of Example 1 was repeated, but using ammonium formate in place of ammonium acetate, and first transferring the working solution emanating from decanter 30 into a container and there heating it to 200° C. before directing it into column 40. This container was heated in series with the boiler 40; the flow rate of steam through this container and through the boiler 40 was also 10,500 kg/h.

The formate was formed in situ by the addition of formic acid.

Via inlet 12, 60 kg/h acetic acid were replaced with 53 kg/h formic acid. The other parameters of the process were identical.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the continuous production of an azine, comprising (i) establishing a loop having an azine reaction medium circulating therein, said loop including an azine reaction zone, means for separating azine final product from said circulating reaction medium, means for heating said reaction medium and for purging water therefrom, and means for recycling heated and purged reaction medium to said azine reaction zone, (ii) introducing hydrogen peroxide, ammonia and a ketone or aldehyde compound into said circulating reaction medium in said azine reaction zone, (iii) withdrawing azine final product thus formed from said circulating reaction medium, (iv) heating said circulating reaction medium to a temperature of at least 130° C., wherein step (iv) is conducted after step (iii), (v) recycling thus heated reaction medium to said azine reaction zone, and (vi), at any point along said loop, introducing a reagent selected from the group consisting of oxyacids, ammonium salts of oxyacids, and anhydrides, esters, amides, nitriles or acyl peroxides of oxyacids into said circulating reaction medium as to essentially maintain the equilibrium of the azine-forming reaction.

2. The process as defined by claim 1, wherein said ketone is acetone, methyl ethyl ketone or methyl isobutyl ketone.

3. The process as defined by claim 1, wherein said azine reaction zone contains an amount of circulating reaction medium ranging from 0.1 to 1 kg per mole of hydrogen peroxide.

4. The process as defined by claim 1, wherein said azine-forming reaction is carried out at a temperature ranging from 30° to 70° C.

5. The process as defined by claim 1, wherein the heating in step (iv) of said circulating reaction medium is effected at a temperature ranging from 150° C. to 250° C.

6. The process as defined by claim 5, wherein the heating in step (iv) is effected at a temperature ranging from 170° to 230° C.

7. The process as defined by claim 5, comprising simultaneously carrying out the steps (iii) and (iv) in a distillation zone.

8. The process as defined by claim 1 further comprising hydrolyzing said azine final product into hydrazine hydrate.

9. The process as defined by claim 8, further comprising recycling carbonyl compound product of hydrolysis to said azine reaction zone.

10. The process as defined by claim 1, wherein said reagent is at least one amide, ammonium salt or nitrile.

11. The process as defined by claim 1, wherein said reagent is acetic acid, formic acid, phenylarsonic acid or cacodylic acid.

12. The process as defined by claim 1, wherein said reagent is a carboxylic acid.

13. The process as defined by claim 1 said circulating reaction medium comprising an aqueous solution, an alcoholic solution, or a mixed aqueous/alcoholic solution.

14. The process as defined by claim 13, said circulating reaction medium comprising ammonia.

15. The process as defined by claim 1, wherein the amount of said reagent is contained in said circulating reaction medium in said azine reaction zone is at most 1% by weight.

16. The process as defined by claim 1, further comprising purging high boiling impurities from said circulating reaction medium.

17. The process as defined by claim 1, further comprising introducing a catalytically effective amount of an azine-forming catalyst into said circulating reaction medium.

18. The process as defined by claim 17, said catalyst comprising a phosphate, phosphite, phosphoriate, polyphosphate, pyrophosphate, arsenate, phenylarsenate, cacodylate, bicarbonate, antimonate, stannate or an ammonia or an alkali metal sulfate.

19. The process as defined by claim 18, said catalyst comprising an alkali metal phosphate or ortho-phosphate.

20. The process as defined by claim 1, comprising (ii) introducing 0.2 to 5 moles of ketone or aldehyde compound and 0.1 to 10 moles of ammonia per mole of hydrogen peroxide.

21. The process of claim 1, further comprising purging water from said circulating reaction medium to maintain the volume thereof essentially constant.

22. The process of claim 21, wherein the step of purging water from said circulating reaction medium is conducted after the step (iii).

23. The process of claim 1, wherein the step (iii) is conducted downstream of said azine reaction zone.

* * * * *